United States Patent
Zochbauer et al.

(10) Patent No.: US 6,452,182 B1
(45) Date of Patent: Sep. 17, 2002

(54) PHOTOMETER WITH NON-DISPERSIVE INFRADED ABSORPTION SPECTROSCOPY (NDIR) FOR MEASURING SEVERAL CONSTITUENTS

(75) Inventors: Michael Zochbauer, Oberursel; Walter Fabinski, Kriftel; Thomas Liedtke, Bad Homburg; Michael Moede, Schwalbach; Siegfried Vogt, Morfelden-Walldorf, all of (DE)

(73) Assignee: ABB Patent GmbH, Mannheim (DE)

( * ) Notice: Subject to any disclaimer, the term of this patent is extended or adjusted under 35 U.S.C. 154(b) by 0 days.

(21) Appl. No.: 09/485,987
(22) PCT Filed: Aug. 12, 1998
(86) PCT No.: PCT/DE98/02412
§ 371 (c)(1),
(2), (4) Date: Feb. 17, 2000
(87) PCT Pub. No.: WO99/09391
PCT Pub. Date: Feb. 25, 1999

(30) Foreign Application Priority Data

Aug. 18, 1997 (DE) .......................... 197 35 719
Nov. 27, 1997 (DE) .......................... 197 52 508

(51) Int. Cl.[7] ................................. G01J 5/02
(52) U.S. Cl. ...................... 250/344; 356/437
(58) Field of Search .............. 250/343, 344, 250/345, 349; 356/437

(56) References Cited

U.S. PATENT DOCUMENTS

| 4,332,770 A | * | 6/1982 | Ishida et al. | 422/78 |
| 4,885,469 A | * | 12/1989 | Yamagishi et al. | 250/345 |
| 5,055,688 A | * | 10/1991 | Fabinski | 250/344 |
| 5,340,542 A | * | 8/1994 | Fabinski et al. | 250/344 |

FOREIGN PATENT DOCUMENTS

| JP | 7-167784 | * | 7/1995 | 250/343 |
| JP | 7-218434 | * | 8/1995 | 250/343 |

* cited by examiner

Primary Examiner—Huy Mai
(74) Attorney, Agent, or Firm—Michael M. Rickin

(57) ABSTRACT

A photometer for measuring gas components. The photometer has an infrared radiator with radiator modulation, a measuring cell with a measurement and comparison chamber, and a detector which absorbs optopneumatically onto the gas component X, that is filled with gas component X. In order in the case of a photometer of this type to render it possible for a plurality of gas components to be measured with high accuracy and the smallest possible outlay in apparatus, at least one further detector is arranged downstream of the first detector. For the purpose of measuring the gas component Y the further detector is filled with its isotope Y*, and the first detector is optically transparent with regard to the further gas component Y* to be measured or the characteristic absorption bands thereof.

29 Claims, 3 Drawing Sheets

Figure 1:
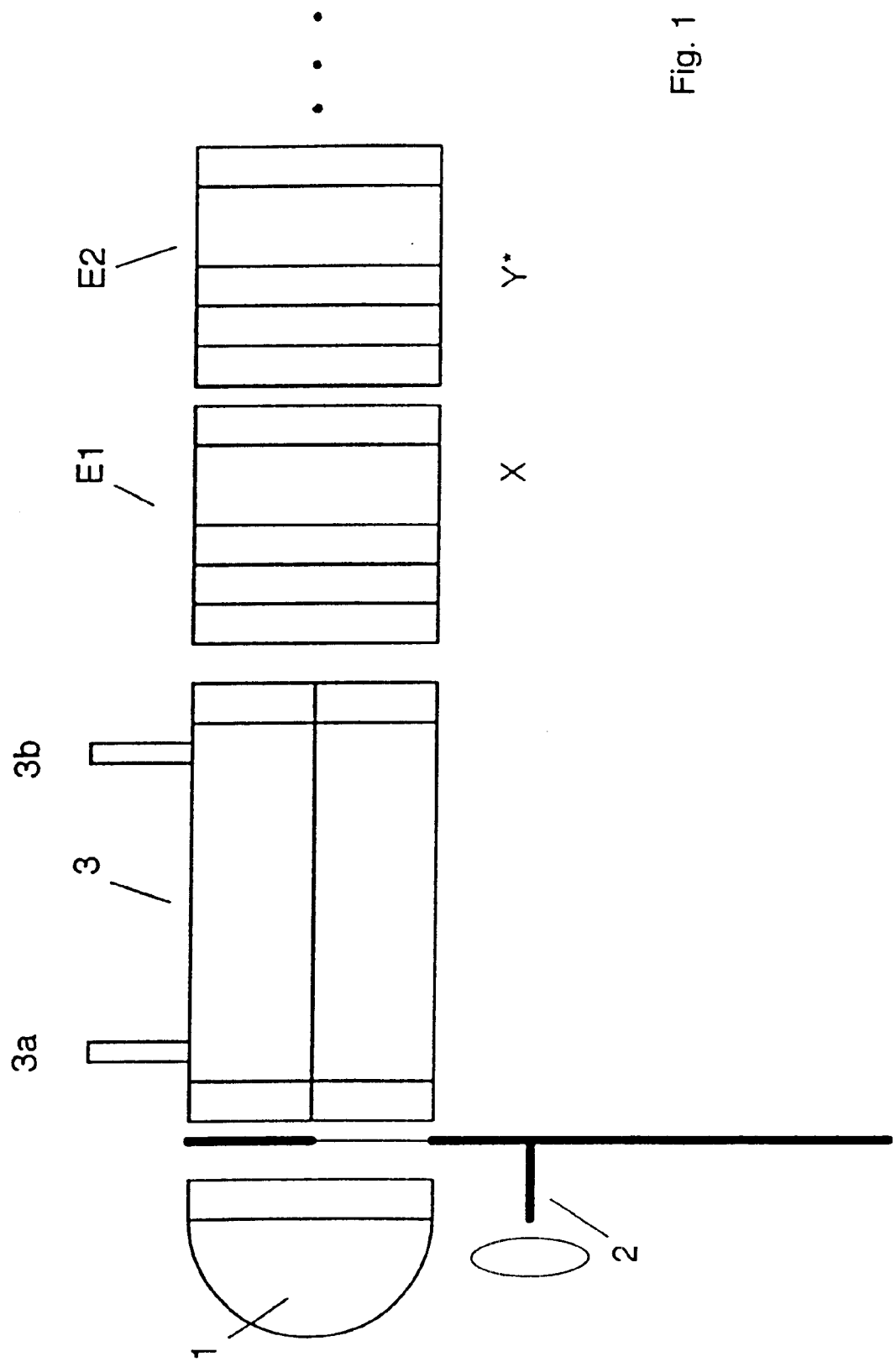

PHOTOMETER WITH NON-DISPERSIVE INFRADED ABSORPTION SPECTROSCOPY (NDIR) FOR MEASURING SEVERAL CONSTITUENTS

DESCRIPTION

The invention relates to a photometer using the non-dispersive infrared spectroscopy method, NDIR method for short, having a measuring cell, an infrared radiator with radiator modulation, the measuring cell consisting of a measurement and comparison chamber, and having at least one optopneumatic detector, in accordance with the preamble of Patent Claim 1.

The output characteristic of absorption photometers, which also include the NDIR photometer, obeys the Lambert-Beer law. The desired linear relationship between concentration and output current requires electronic measures forlinearization. In addition to pure absorption, however, there is also extinction along the beam path through the cell. To this extent, the measuring range is limited in general by a maximum product of cell length and concentration. Here, pure extinction is the non-selective general attenuation of radiation by gases or solids. Extinction too effects attenuation of the original signal and therefore simulates absorption. To this extent, the cell lengths cannot be selected arbitrarily.

Moreover, optopneumatic photometers are known whose gas-filled detectors can be connected in series, with the result that it is possible to determine two or more components simultaneously with only one measuring cell. However, this procedure fails in the case of very different measuring ranges, because of the abovementioned problem with the output characteristic. This is the case, for example, with the more or less routine analysis of combustion gases. The aim here is frequently to determine the generally low CO concentration (100 ppm) and the high $CO_2$ concentration (15% by volume). It is usually necessary to construct two beam paths with different cell lengths in order to solve this problem.

Furthermore, there is known from DE 44 19 458 a method for measuring the purity of $CO_2$ in which the measurement of natural $CO_2$ is limited to the absorption band f the isotope $^{13}CO_2$. In this case, the method is tuned and configured exclusively such that only purity measurements of this one measuring component can be carried out.

The problem is thus that it is mostly necessary to use a plurality of measuring cells in the case of a desired measurement of a plurality of components, since the at least two components to be measured occur in different measuring ranges. One example of this is the already known method of using NDIR spectroscopy to measure the ratio of $^{12}CO_2$ and $^{13}CO_2$ in separate beam paths. Since the concentrations to be measured differ by approximately 1:100, each channel is provided with a dedicated measuring cell differing in length. The different lengths are selected in order to render it possible to linearize the output characteristics, which sag in accordance with the Lambert-Beer law. Both cells are charged in parallel with measuring gas. As a result of the measurement, the individual components, and also the quotient of $^{13}CO^2/^{12}CO_2$ are output. Owing to the fact that the cells can be charged with measuring gas in a fashion which is not exactly simultaneous, when a quotient is formed during an online measurement of, for example, respiratory air unavoidable dynamic errors occur which cause large dynamic deviations when conducting online measurement of a proband. Added to this, again, is the overall problem, already outlined, of handling isotope ratios of an at least chemically identical gas component.

Moreover, the two measurement results must, again, be further computed in order to obtain some degree of mutual correspondence, since it is, after all, one and the same measuring gas which is concerned, even if it consists of a plurality of components. The reason why this is so critical is that the NDIR method is an absorption method. That is to say, the higher the concentration in the measuring gas of the component actually to be measured, the higher the specific absorption inside the gas. That is to say, given high concentrations all that remains is a small residual signal which reaches the detector. The remaining radiation intensity is, however, decisive, again, for producing the measuring effect, since the detectors depend in this gas-filled form on the optopneumatic effect. That is to say, with ever larger concentrations the residual signal paradoxically becomes ever smaller, and thus also ever less accurate. By contrast, low concentrations can be measured accurately because owing to the low concentration the specific absorption inside the measuring cell is also correspondingly low, with the result that a relatively high light signal remains to excite the detector. This problem, which essentially reflects the Lambert-Beer law is important in measuring a plurality of components.

It is therefore the object of the invention to render it possible to measure a plurality of components with high accuracy and the smallest possible outlay on apparatus.

According to the invention, the object adopted is achieved by means of the characterizing features of Patent Claim 1 in the case of an NDIR photometer of the generic type.

Further advantageous refinements of the invention are reproduced in the dependent claims.

The aim of this invention is to measure a plurality of components without the disadvantages of the measurement techniques of this type which are currently employed. By contrast therewith, it is to be possible for this measurement to be implemented simply and cost-effectively. The aim in this case is to use only a single measuring cell in order to achieve the same dynamic characteristic for the various measuring components. It is essential here to use a plurality of detectors which are connected in series and measure the individual gas components selectively. The gas components and/or the correspondingly selected absorption bands possible in this case must be selected here such that each detector exercises maximum absorption for the measuring component which it is to measure, and must be correspondingly transparent for the component which is to be detected in the downstream detector. Since the detectors enclose only relatively low gas volumes, the extinctions effected thereby from one detector to the other are negligible or at least known, and therefore capable of compensation.

The embodiment according to the invention assumes that the measuring component is present in its natural isotope abundance. Thus, it is known that natural $CO_2$ consists of approximately 98.9% $^{12}CO_2$ and a fraction of approximately 1.1% $^{13}CO_2$. Similar relationships hold for other gases such as CO, $CH_4$ and others. The isotope ratio is sufficiently constant for most technical processes, with the result that it is possible, for example, to measure $^{13}CO_2$ instead of $^{12}CO_2$. If there is thus a change in the composition of $CO_2$, it is a proportional, representative change in the largely constant low fraction of $^{13}CO_2$, as well. However, it is important that the concentration present here is approximately 100 times lower than when $CO_2$ overall or $^{12}CO_2$ is measured. Consequently, absorption as such in the measuring cell is so low, again, that as large as possible a residual light signal reaches the detector. This means, therefore, that when the detector measures $CO_2$ represented by $^{13}CO_{12}$ it measures in a clearly more favourable branch of the Lambert-Beer law. A second beam path with a second cell for a second measuring component. The photometer according to the invention operates optimally for those gas components in the case of which, for example, carbon is contained as chemical ligand in the molecules. It is then therefore possible the way according to the invention of the representative measurement of $^{13}CO_2$ as a representative for $CO_2$ also to be applied generally to other molecules such as, for example, CO or $CH_4$ and others. In this way, the transmittance ratios are then selected such that the corresponding isotope absorption bands are shifted with respect to those of the basic element. Only thus is it possible to implement this mode of procedure in general. Thus, for example, in a gas mixture of X and Y the smaller fraction X, for example, would mean that the detector measures directly, that is to say not in an isotope-selective fashion, and the detector connected downstream thereof would be filled with Y* and thus measure the isotope relating to Y as a representative relating to the Y concentration. The only important point in this case is that the first detector should be transparent with respect to the Y* band in this frequency range; that is to say the absorption band of X is not permitted to coincide with that of Y*. This can also be extended to gas mixtures consisting, for example, of X, Y, Z and W, in which the detector X measures a basic concentration of X, again not in an isotope-selective fashion, and then three, series-connected, further detectors are arranged, of which one Y*, one Z* and the last is filled with W*. Here again, the only important point in this case is that the detectors respectively connected upstream are transparent with respect to the downstream detectors and their absorption bands, that is to say do not mutually overlap. The extinction produced upon passage through the detector window and upon passage through the gas section overall can be predetermined in this case very effectively, for example with the aid of calibration cells which are to be inserted and can be used to determine the individual extinction values.

In the embodiment according to the invention in accordance with Claim 2, the aim is specifically to measure the isotope ratio of $^{13}CO_2$ and $^{12}CO_2$, with the object of using this configuration according to the invention to render it possible to measure in a modal fashion. This simultaneously counters the problem, already described above, that two measuring beam paths cannot be adjusted to pure online measurement. This is achieved by virtue of the fact that only one measuring cell is used for measuring both the $^{13}CO_2$ and the $^{12}CO_2$. A filter cell filled with $^{12}CO_2$ is located in a way according to the invention in series with the measuring cell. Arranged downstream of said filter cell is a first detector, filled with $^{12}CO_2$, for measuring $^{12}CO_2$, and arranged downstream thereof, is, again, a second detector, filled with $^{13}CO_2$, for measuring $^{13}CO_2$. No additional filtering is undertaken between the two detectors, E1 and E2.

As already mentioned above, in order to reduce the sagging of the detector characteristic the filter cell is introduced upstream of the first detector, which is filled with $^{12}CO_2$. Said filter cell is filled with $^{12}CO_2$, and attenuates the dominant $^{12}CO_2$ main bands to such an extent that it is possible to work with the downstream $^{12}CO_2$ detector in a flatter and thus more favourable region of the characteristic. The filter cell simultaneously reduces the cross-sensitivity of $^{12}CO_2$ to the $^{13}CO_2$ channel. Only one calibration cell is used for calibration purposes, being filled with a mixture of $^{12}CO_2$ and $^{13}CO_2$ and being capable of being swivelled in between the filter cell and the first detector.

A further, and thus third embodiment of the invention, as specified in Claim 3, firstly uses a design as in the second embodiment, but in this case the detectors are exchanged and there is arranged between the detectors an interference filter which passes only the overtone bands of the gas component active in the downstream detector. The arrangement of a filter cell as in the second exemplary embodiment is not mandatory, however, because $^{12}CO_2$ is not measured until the last detector downstream, and only the overtone bands are still used for this purpose, after all. These overtone bands are left with just one absorption, which is approximately 100 times weaker than that of the main bands. Consequently, this is situated far in the linear region with regard to the detector characteristic.

Figure 2:
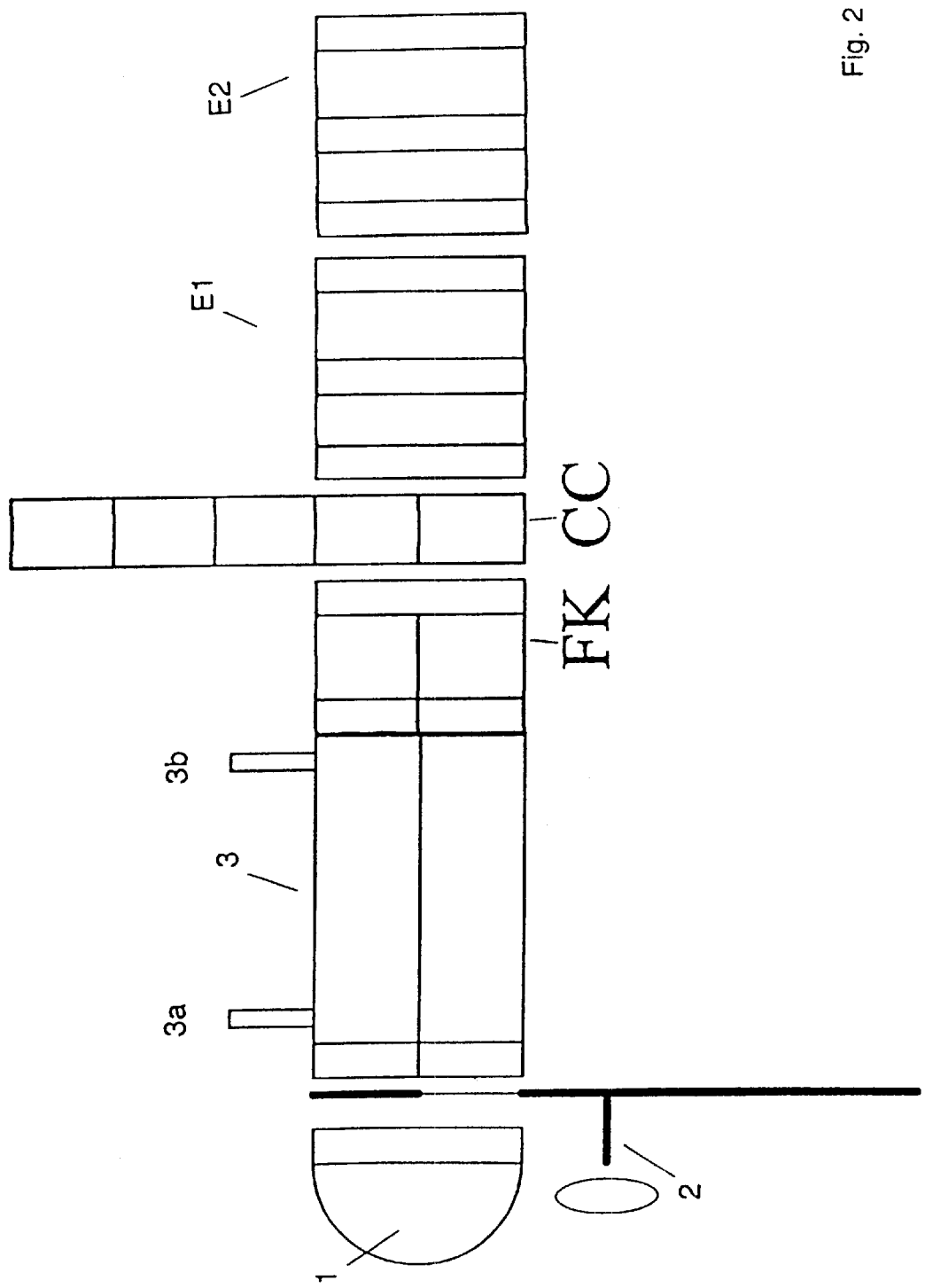
Figure 3:
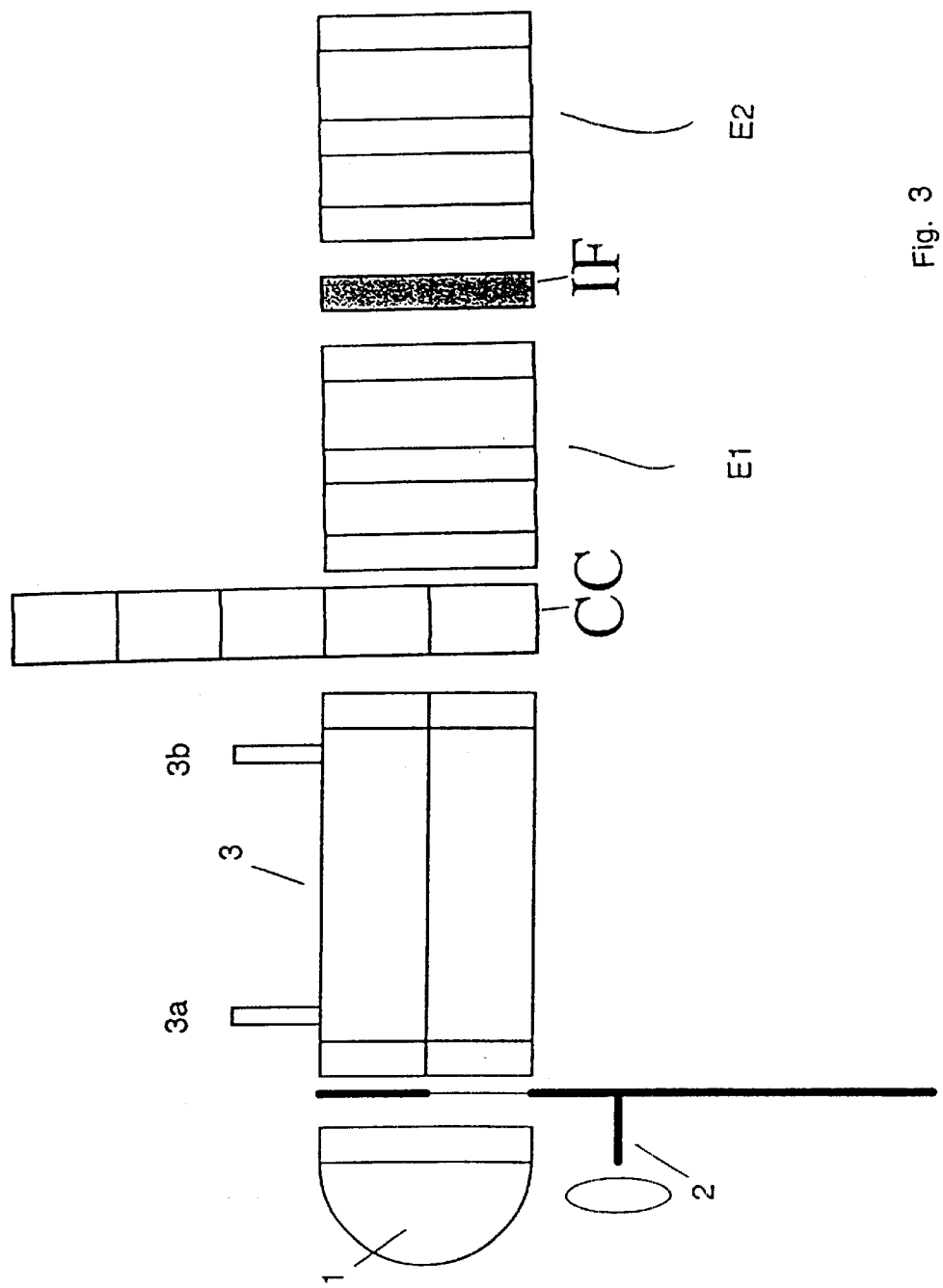

The three embodiments of an NDIR photometer arrangement with a detector arrangement and filling according to the invention are shown in the drawing, in which:

FIG. 1 shows the design according to the invention in accordance with claim 1,

FIG. 2 shows the design according to the invention in accordance with claim 2, and FIG. 3 shows the design according to the invention in In accordance with the design according to FIG. 1, the photometer or the photometer arrangement essentially comprises a radiation source 1, a radiation modulator 2 and a measuring cell 3. The latter is provided with a gas inlet 3a and a gas outlet 3b such that measuring gas can be led in and, after flowing through the measuring cell, be led off again at the gas outlet.

Downstream thereof is the first optopneumatic detector E1, which is filled with the gas component X, and then also measures the latter. A further detector E2 is arranged downstream of the first detector E1. The further detector E2 for measuring the gas component Y is filled with its isotope Y*. That is to say, for the gas component Y it measures representatively the concentration of Y* and in so doing deduces the concentration of Y. For this purpose, the first detector is optically transparent with respect to the further gas component Y* to be measured or the characteristic absorption bands thereof.

It is possible to provide further detectors for further gas components, which are then simply lined up downstream of the other detectors.

For this purpose, a further detector (not represented here) is arranged downstream of the preceding detector for the purpose of measuring at least one further gas component Z. It is not mandatory, though helpful, in this case, as well, to fill the further detector in the same way with the isotope Z* of the gas component Z to be measured, if there would otherwise be linearization problems. The preceding detectors are optically transparent with regard to the further gas component Z* to be measured or the characteristic absorption bands thereof. That is to say, the further gas components are also not measured directly, but representatively via their isotopes. Of course, the composition of the filling of the calibration cell is to be coordinated therewith.

As likewise not represented in the drawing, it is possible to provide a calibration cell which can be introduced between the measuring cell 3 and the first detector E1, and which is filled with a mixture of X+Y* or of X+Y*+Z* or of X+Y*+Z*+ . . .

In accordance with the design according to FIG. 2, the NDIR photometer arrangement likewise has only one measuring beam path.

In the embodiment according to the invention in accordance with Claim 2, the specific purpose is to measure the isotope ratio of $^{13}CO_2$ and $^{12}CO_2$. The aim set in this case is the possibility of modal measurement, online measurement being in the foreground. This is achieved, on the one hand, by virtue of the fact that, here as well, just one measuring cell is used to measure both $^{13}CO_2$ and $^{12}CO_2$. Located in series with the measuring cell is a filter cell FK filled with $^{12}CO_2$. Arranged downstream thereof is a first detector E1, filled with $^{12}CO_2$, for measuring $^{12}C_2$, and arranged downstream thereof is a second detector, filled with $^{13}CO_2$, for measuring $^{13}CO_2$. The possibility of linearizing the large measuring range or of shifting the measuring into the linear range of the measuring curve is achieved by virtue of the fact that a filter cell FK is arranged upstream of the $^{12}CO_2$ receiver E1. Said filter cell FK then attenuates the radiation to such an extent that the downstream $^{12}CO_2$ detector E1 operates in the linear section of its measuring curve. The filter cell FK simultaneously reduces the $^{12}CO_2$ cross-sensitivity to the $^{13}CO_2$ channel. Use is made for calibration purposes of only one calibration cell CC, which is filled with a mixture of $^{12}CO_2$ and $^{13}CO_2$, and can be swiveled into the beam path if required.

A third and last embodiment of the invention is shown in FIG. 3. In this case, the design is firstly as in FIG. 1 or 2, the filter cell now no longer being mandatory and, moreover, the detectors being exchanged. That is to say the $^{13}CO_2$ detector is now at the front, and the $^{12}CO_2$ detector is only behind it. In the drawing, this means that the detector E1 is now filled with $^{13}CO_2$, and the detector E2 is filled with $^{12}CO_2$. There is an interference filter IF between the two detectors E1 and E2. In the case when a filter cell is arranged upstream of the first detector E1, said cell is then also filled with $^{12}CO_2$ and reduces the cross-sensitivity. The said interference filter IF is designed such that it passes only the radiation in the region of the overtone bands of the $^{12}CO_2$ for the downstream $^{12}CO_2$ detector E2. Thus, it is possible using a simple design to undertake a very efficient and very accurate measurement of the $^{12}CO_2/^{13}CO_2$ ratio, because in both gas components measurement is made in the linear region of the respective optopneumatic detectors E1 and E2.

As described above, the capacity to linearize the large measuring range is achieved by virtue of the fact that the said interference filter IF is arranged upstream of the $^{12}CO_2$ detector E2. Said filter IF passes only radiation in the region of the overtone band of $^{12}CO_2$, which, as already mentioned above, has only a substantially weaker extinction than that of the fundamental at 4.25 $\mu$m. The passband of this filter is 2.0 $\mu$m or 2.7 $\mu$m in the present exemplary embodiment. Thus, in the region of the overtones the absorption or extinction is less than in the region of the main band. In the case of $^{12}CO_2$, this is only a hundredth of the absorption in the main band. In this case, measurement is carried out only in the region of the Lambert-Beer law, which is linear and can therefore be effectively calibrated.

What is claimed is:

1. Photometer for measuring gas components, having an infrared radiator with radiator modulation and a measuring cell with a measurement and comparison chamber, and having a first detector which is filled with a gas component X characterized in that for the purpose of measuring a plurality of gas components at least one further detector (E2) is arranged downstream of the first detector (E1), in that for the purpose of measuring a gas component Y the further detector (E2) is filled with an isotope Y* of said gas component Y, and in that the first detector (E1) is optically transparent with regard to the isotope Y* to be measured or the characteristic absorption bands of said isotope Y*.

2. Photometer for measuring gas components according to claim 1, characterized in that at least one further detector (E3, E . . . ) is arranged downstream of the preceding detector (E2, . . . ) for the purpose of measuring at least one further gas component Z, and in that the at least one further detector (E3, E . . . ) is filled either with the gas component Z or its isotope Z*, and the preceding detectors are optically transparent with regard to the further gas component Z or Z* to be measured or the characteristic absorption bands of said further gas component Z or its isotope Z*.

3. A photometer for measuring gas components according to claim 2 characterized in that it is possible to introduce upstream of the detectors (E1, E2, . . . ) a calibration cell which is filled with a mixture of X+X* or of X+Y* or of X+Y*+Z, Z* or of X+Y*+Z, Z*+ . . . or X1*+X2*.

4. A photometer for measuring gas components according to claim 1 characterized in that it is possible to introduce upstream of the detectors (E1, E2, . . . ) a calibration cell which is filled with a mixture of X+X* or of X+Y* or of X+Y*+Z, Z* or of X+Y*+Z, Z*+ . . . or X1*+X2*.

5. A photometer for measuring gas components or isotope ratios of gas components according to claim 1 characterized in that an interference filter having a pass region at the overtone bands of the gas component detected by the at least one further detector is interposed between said first detector and said at least one further detector.

6. A photometer for measuring gas components or isotope ratios of gas components according to claim 1 characterized in that a filter cell is arranged between the measuring cell and the first detector.

7. A photometer for measuring gas components or isotope ratios of gas components according to claim 6, characterized in that the filter cell is filled with the gas component X or X1*.

8. A photometer for measuring gas components or isotope ratios of gas components according to claim 7, characterized in that the gas component X1* is $^{12}CO_2$.

9. A photometer for measuring gas components or isotope ratios of gas components according to claim 7, characterized in that the filter cell is structurally integrated in the measuring cell.

10. A photometer for measuring gas components or isotope ratios of gas components according to claim 1 characterized in that the component X1* is $^{12}CO_2$ and the component X2* is $^{13}CO_2$.

11. A photometer for measuring gas components or isotope ratios of gas components according to claim 1 characterized in that the component X1* is $^{12}CO_2$, and the component X2* is $^{13}CO_2$, and the component Y* is the isotope of a further measuring gas component.

12. Photometer for measuring gas components or isotope ratios of gas components, having an infrared radiator with radiator modulation and a measuring cell with a measurement and comparison chamber, and having a first detector which is filled with an isotope X1* characterized in that for the purpose of measuring a plurality of gas components at least one further detector (E2) is arranged downstream of the first detector (E1), in that for the purpose of measuring an isotope X* the further detector (E2) is filled with an isotope X2*, and in that the first detector (E1) is optically transparent with regard to the isotope X2* to be measured or the characteristic absorption bands of said isotope X2*.

13. A photometer for measuring gas components according to claim 12 characterized in that it is possible to introduce upstream of the detectors (E1, E2, . . . ) a calibration cell which is filled with a mixture of X+X* or of X+Y* or of X+Y*+Z, Z* or of X+Y*+Z, Z*+ . . . or X1*+X2*.

14. A photometer for measuring gas components or isotope ratios of gas components according to claim 12 characterized in that an interference filter having a pass region at the overtone bands of the gas component detected by the at least one further detector is interposed between said first detector and said at least one further detector.

15. A photometer for measuring gas components or isotope ratios of gas components according to claim 12 characterized in that a filter cell is arranged between the measuring cell and the first detector.

16. A photometer for measuring gas components or isotope ratios of gas components according to claim 15, characterized in that the filter cell is filled with the gas component X or X1*.

17. A photometer for measuring gas components or isotope ratios of gas components according to claim 16, characterized in that the gas component X1* is $^{12}CO_2$.

18. A photometer for measuring gas components or isotope ratios of gas components according to claim 16, characterized in that the filter cell is structurally integrated in the measuring cell.

19. A photometer for measuring gas components or isotope ratios of gas components according to claim 12 characterized in that the component X1* is $^{12}CO_2$ and the component X2* is $^{13}CO_2$.

20. A photometer for measuring gas components or isotope ratios of gas components according to claim 12 characterized in that the component X1* is $^{12}CO_2$, and the component X2* is $^{13}CO_2$, and the component Y* is the isotope of a further measuring gas component.

21. Photometer for measuring gas components or isotope ratios of gas components, having an infrared radiator with radiator modulation and a measuring cell with a measurement and comparison chamber, and having a detector which is filled with an isotope X1* characterized in that at least first and second detectors (E1, E2) are provided for the purpose of measuring a plurality of gas components, in that the first detector (E1) is filled with the isotope X2* for the purpose of measuring isotope X2*, and the second detector (E2) is filled with the isotope X1* for the purpose of measuring the isotope X1*, and in that there is arranged between the at least first and second detectors (E1, E2) an interference filter which essentially passes only radiation in the region of the overtone bands of X1* such that said second detector operates in a linear region of the Lambert-Beer law.

22. A photometer for measuring gas components according to claim 21 characterized in that it is possible to introduce upstream of the detectors (E1, E2, . . . ) a calibration cell which is filled with a mixture of X+X* or of X+Y* or of X+Y*+Z, Z* or of X+Y*+Z, Z*+ . . . or X1*+X2*.

23. A photometer for measuring gas components or isotope ratios of gas components according to claim 21 characterized in that an interference filter having a pass region at the overtone bands of the gas component detected by the second detector is interposed between the first detector and the second detector.

24. A photometer for measuring gas components or isotope ratios of gas components according to claim 21 characterized in that a filter cell is arranged between the measuring cell and the first detector.

25. A photometer for measuring gas components or isotope ratios of gas components according to claim 24, characterized in that the filter cell is filled with the gas component X or X1*.

26. A photometer for measuring gas components or isotope ratios of gas components according to claim 25, characterized in that the gas component X1* is $^{12}CO_2$.

27. A photometer for measuring gas components or isotope ratios of gas components according to claim 25, characterized in that the filter cell is structurally integrated in the measuring cell.

28. A photometer for measuring gas components or isotope ratios of gas components according to claim 21 characterized in that the component X1* is $^{12}CO_2$ and the component X2* is $^{13}CO_2$.

29. A photometer for measuring gas components or isotope ratios of gas components according to claim 21 characterized in that the component X1* is $^{12}CO_2$, and the component X2* is $^{13}CO_2$, and the component Y* is the isotope of a further measuring gas component.

* * * * *